United States Patent [19]
Waggoner

[11] Patent Number: 5,360,338
[45] Date of Patent: Nov. 1, 1994

[54] PORTABLE STERILIZABLE WATER SUPPLY FOR DENTAL APPLIANCES

[75] Inventor: Mark B. Waggoner, Plano, Tex.

[73] Assignee: Waggoner Family Corporation, Plano, Tex.

[21] Appl. No.: 943,284

[22] Filed: Sep. 10, 1992

[51] Int. Cl.[5] .......................................... A61G 17/02
[52] U.S. Cl. .................................................. 433/80
[58] Field of Search ...................... 433/80, 82, 84, 88

[56] References Cited

U.S. PATENT DOCUMENTS

| | | | |
|---|---|---|---|
| 2,420,338 | 5/1947 | Page | 32/28 |
| 3,077,665 | 2/1963 | Saltzman | 32/22 |
| 3,081,542 | 3/1963 | Sherfey | 32/22 |
| 3,237,306 | 3/1966 | Staunt | 433/84 |
| 3,949,753 | 4/1976 | Dockhorn | 128/303 |
| 4,359,317 | 11/1982 | Strohmaier et al. | 433/85 |
| 4,669,453 | 6/1987 | Atkinson et al. | 433/80 |
| 4,958,963 | 9/1990 | Perrault | 408/56 |
| 4,973,247 | 11/1990 | Varnes et al. | 433/85 |
| 5,019,038 | 5/1991 | Linden | 604/49 |
| 5,158,454 | 10/1992 | Viebahn et al. | 433/82 |

Primary Examiner—Gene Mancene
Assistant Examiner—Todd E. Manahan
Attorney, Agent, or Firm—Harris, Tucker & Hardin

[57] ABSTRACT

A compact sterilizable unit has a control box containing internal water and air supply networks and a sterilizable water supply bottle, dental handpiece and dental syringe removably connected to the control box by specially adapted connector fittings. The unit has a retrofit connection to a conventional four hole connector which supplies operating air in response to the conventional dental operatory foot control. Only sterile water is supplied to the patient from the sterile water bottle through the handpiece and syringe. The connection of the handpiece to the control box is through a high temperature resistant sterilizable tubing harness having an expanded sheath construction that does not inhibit bending. Short high temperature resistant tube sections which are strengthened by an expanded shrink fit covering sheath are disclosed. Special high temperature resistant tubing and seals are provided so that the entire unit may be sterilized.

37 Claims, 3 Drawing Sheets

PORTABLE STERILIZABLE WATER SUPPLY FOR DENTAL APPLIANCES

BACKGROUND OF THE INVENTION

1. Field of the Invention

The invention is in the field of supplying sterile water or other sterile dental solutions through dental appliances in a portable standardly connectable unit.

2. Background of the Invention

The dental practice is increasingly concerned with the necessity of maintaining a sterile medical environment for the patient. The dental handpiece is most commonly an air operated turbine driven drill which necessarily includes a misting spray of cooling water to avoid heat buildup from friction generated during the drilling operation. Suction devices and dental syringes are employed to wash down and air dry the work area in the patient's mouth. Conventional dental handpieces and the syringes have extended length tubing harnesses which are connected to a stand mounted near the dentist's chair and supplied with a common source of potable water and pressurized operating air. Coolant and rinse fluids are necessarily introduced into the patient's oral cavity. Many standard dental procedures require exposure of the patient's blood system to these fluids through incisions, root canals and other standard dental operations.

In addition to the fact that the potable water supply is not really sterile, and can itself introduce microbial organisms to the patient, there is an increasingly serious concern about the possibility of cross-contamination occurring from patient to patient in connection with the AIDS epidemic. Many of the dental appliances themselves are not sterilizable. Attempts to sterilize them by soaking in alcohol, for example, are mostly ineffective and the tubing which carries the operating fluid and connectors for the tubing are not sterilizable at all.

It would be highly desirable to provide a portable unit which can be connected to a standard source of compressed air through a conventional standard dental fitting but which can provide a sterile solution through sterilizable dental appliances for use as a coolant and rinse in order to provide a substantially sterile environment for each individual patient, and to do so by means of a truly compact portable unit which is conveniently and easily movable from dental station to dental station within a dentist's office and to and from effective sterilizing equipment.

SUMMARY OF THE INVENTION

The present invention is a manually portable sterilizable apparatus which is compatible with the usual and customary equipment in a dentist's office such that it may be hooked up to the conventional standard source of operating air by means of a standard connector which is available at each dental station in the office. The compact apparatus is easily movable from dental station to dental station and to and from sterilizing equipment in order to deliver substantially sterile operating fluids to dental appliances which are modified to withstand repeated autoclaving without noticeable deterioration.

The apparatus comprises a separately sterilizable water supply bottle having a tubing harness for delivery of water through the tubing, the tubing harness having an end portion and a connector on the end of the end portion which may detachably engage the water supply fitting on a control box to establish air and water flow passages between the sterilizable bottle and the control box. A separate sterilizable control box is connectable to a conventional source of dental operating air by means of a standard connector.

An internal air supply network interconnects the water supply fitting and at least one fitting for at least one detachable dental appliance such as a dental handpiece and/or a dental syringe, both of which are separately sterilizable. The fitting for at least one detachable dental appliance is in fluid communication with an internal fluid supply network connecting the water supply fitting with the fitting for the at least one detachable dental appliance wherein sterile water from the water supply bottle can be supplied to the dental appliance fitting in response to pressurized operating air applied to the air supply network. The dental handpiece and the dental syringe are standard conventional dental appliances which have been modified by use of special material for the "O" rings and any other seals and provided with a tubing harness fabricated from a material which is selected for useful operation after repeated autoclaving. The dental handpiece is a modem high speed air turbine driven appliance which has passages for coolant mist.

The internal air supply network has a main branch tube in fluid communication with the dental appliance fitting for a dental handpiece or another similar fitted appliance. It has a junction from the main air branch having a first secondary branch tube in fluid communication with the water supply fitting for simultaneously supplying operating air to the dental appliance fitting and the water supply fitting to simultaneously drive the turbine in the dental handpiece and pressurize sterile water in the water supply bottle when its tubing harness is connected to the water supply fitting by a quick connect air and water coupling. Sterile water from the water supply bottle is delivered through its tubing harness and water supply fitting to the internal water supply network.

The internal water supply network has a sterile water supply tube connected to the water supply fitting in fluid communication through a branch tube with a fitting mounted on the control box for another dental appliance which preferably is a dental air/water syringe. A one-way flow valve in the branch tube leading to the fitting for the syringe is adapted to permit water supply to the dental syringe through the fitting while blocking reverse fluid flow into the fluid supply network. The dental air/water syringe contains hand operated switches and internal valves connected to the tubing harness for the dental air/water syringe which may be depressed to deliver air or sterile water from the syringe when the tubing harness is connected to the fitting for another dental appliance by a quick connect coupling on the end of the harness. Operating air is supplied to the dental air/water syringe by means of a syringe air branch tube leading from the junction connected to the main air branch tube which supplies air to the water supply bottle. The syringe air tube is in fluid communication with the dental syringe through the fitting for another appliance and the syringe tubing harness. When pressurized operating air is supplied to said junction, it is available to the syringe along with sterile water from the bottle which is forced into the internal water supply network by pressure from the same junction. A special effect is provided by the junction in the internal air supply network which simultaneously provides operating air to the sterile water bottle and syringe having a one-way flow valve which permits air to flow in one direction, in combination with a vent tube leading from said junction through a toggle switch which opens or closes the vent tube. When the vent is closed, pressurized air is retained in the sterile water bottle even when the incoming operating air pressure is shut off, so that water continues to be supplied to the dental syringe for use as a rinse at the end of a dental operation and the internal water supply network remains pressurized to prevent any possibility of backflow through tubing lines leading to the sterile water bottle.

The dental handpiece is detachably connected through a fitting directly to the air supply network and indirectly to the fluid supply network through a pilot valve operated by the air supply network. The internal water supply network has a tube leading from the water supply fitting to a normally closed air operated pilot valve in the water supply network which controls the flow of sterile water from the sterilizable water bottle through the pilot valve. Coolant water for the dental handpiece is supplied by tubing in fluid communication therewith through a needle valve to control the amount of flow, but only when the air operated pilot valve is open. Air to operate the pilot valve is supplied through a pilot branch extending from a junction in the main air supply which leads to the dental handpiece. A switch in the main air supply line ahead of the junction having the branch leading to the pilot valve is openable and closeable to start or stop the flow of air to the pilot branch which starts or stops the flow of sterile water at the pilot valve. This arrangement uniquely permits the simultaneous starting and stopping of the flow of operating air and sterile coolant water to the dental handpiece connected to the control box.

The air junction having the pilot valve also has a chip air line leading through the tubing harness to the handpiece, all of which is ultimately turned on or off by means of a foot rheostat at the master dental control unit. The pilot valve has a chamber for the sterile water which remains under pressure even when the main air supply to the control box is disconnected, provided the toggle switch is in the closed position so that residual air is trapped in the air supply to the sterile water bottle. This arrangement prevents even the remote possibility of backflow from the dental handpiece into the sterile water supply. Operation of the foot switch in the main air supply line on the control box upstream of the pilot branch junction also permits the dental handpiece to be turned off while pressurized air remains available to the sterile water bottle and the dental syringe when operating air to the control box is supplied by depressing the foot rheostat on the master dental control unit.

The present invention can advantageously be connected to an existing dental unit by a standard connector and operated by the conventional dental air supply to supply sterile water instead of the normal coolant water supply. Pressurized dental operating air can be obtained from a standard dental "3-hole" or "4-hole" dental handpiece tubing connector leading to a modulated air source which is controlled by a foot rheostat pedal. This connection can be repeatedly connected and detached in any dental operating room.

A special male style "4-hole" connector prior to the portable control box is connected by means of the main air supply tube and the return air tube to said control box. This connector allows for the convenient, simple direct connection to the standard dental "4-hole" female dental handpiece tubing connector by means of a connector nut.

The invention advantageously employs an air actuated pilot valve which is a water relay valve. The pilot valve not only acts as a check valve but also immediately stops water outflow when the foot pedal control which provides operating air pressure is released, thus stopping undesirable dripping of coolant fluid upon patients and offering immediate outflow of water and fluid upon command.

The invention offers a large enough fluid volume to complete a dental procedure using a sterile fluid, which can be water or a mix of water or saline with a bacteriostatic or bacteriocidal agent which can offer the enhanced effect of decreasing bacteria in the mouth.

The size and handiness of the equipment of the present invention makes it possible for the dentist to work in their dental operatory room with the same equipment that they normally use and never notice the addition of the inventive system which does not interfere with their operating freedom of movement. They have the same feel to their dental appliances without changing their routine while offering the patient a sterile water-fluid source.

A special male style "4-hole" connector on the proximal end of the tubing harness for the dental handpiece allows for the conveniently simple direct connection and disconnection of said tubings; harness with a standard female "4-hole" connector on the control box.

The invention is preferably constructed of separable autoclavable parts which are connected together to make the whole. Not only are the dental handpiece. and syringe, along with their tubing harnesses, autoclavable between patients, but the control box is very small and separately autoclavable between patients as well. For the first time, the dentist is offered a compact, portable unit which is economical to construct with mostly standardized parts which permits virtually complete and effective sterility for all components so that the dentist can be virtually assured of freedom from cross-contamination when the apparatus is sterilized between patients.

DETAILED DESCRIPTION OF A PREFERRED EMBODIMENT

In the description that follows, like reference numerals will be used to denote the same parts in different Figures of the drawings. Although the term "sterile water" or "water supply fitting:" or similar terms will be used, it is understood that this is broad enough to and does encompass any primarily aqueous fluid or solution that would be useable both as a coolant and rinse in dental practice.

Figures 1, 3:
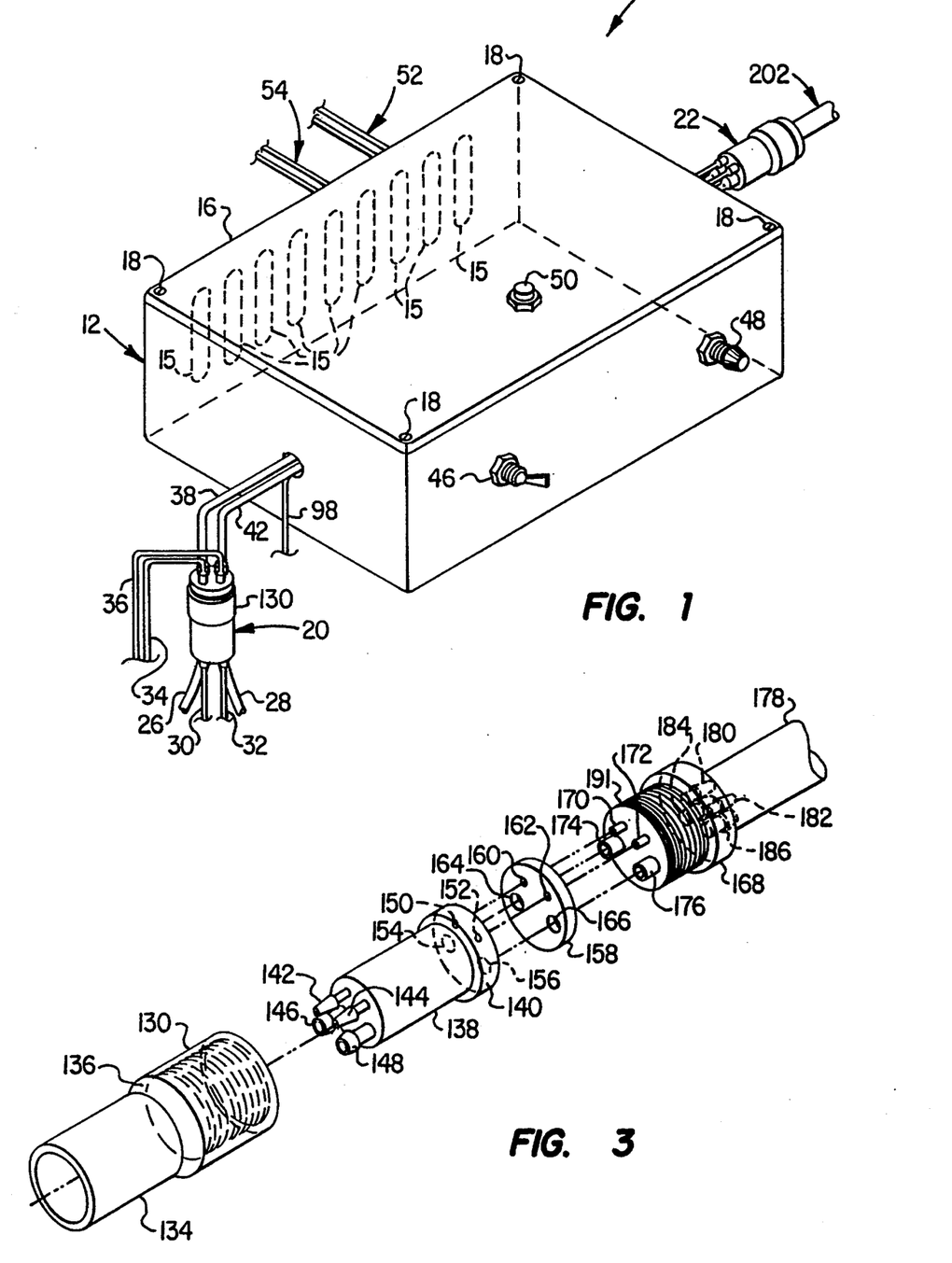
FIG. 1 is a perspective view of a sterilizable control box showing somewhat schematically the connectors for a conventional source of pressurized operating air and a connector for a dental appliance.
FIG. 3 is an exploded perspective view of the connectors shown in FIG. 1.
Figure 2:
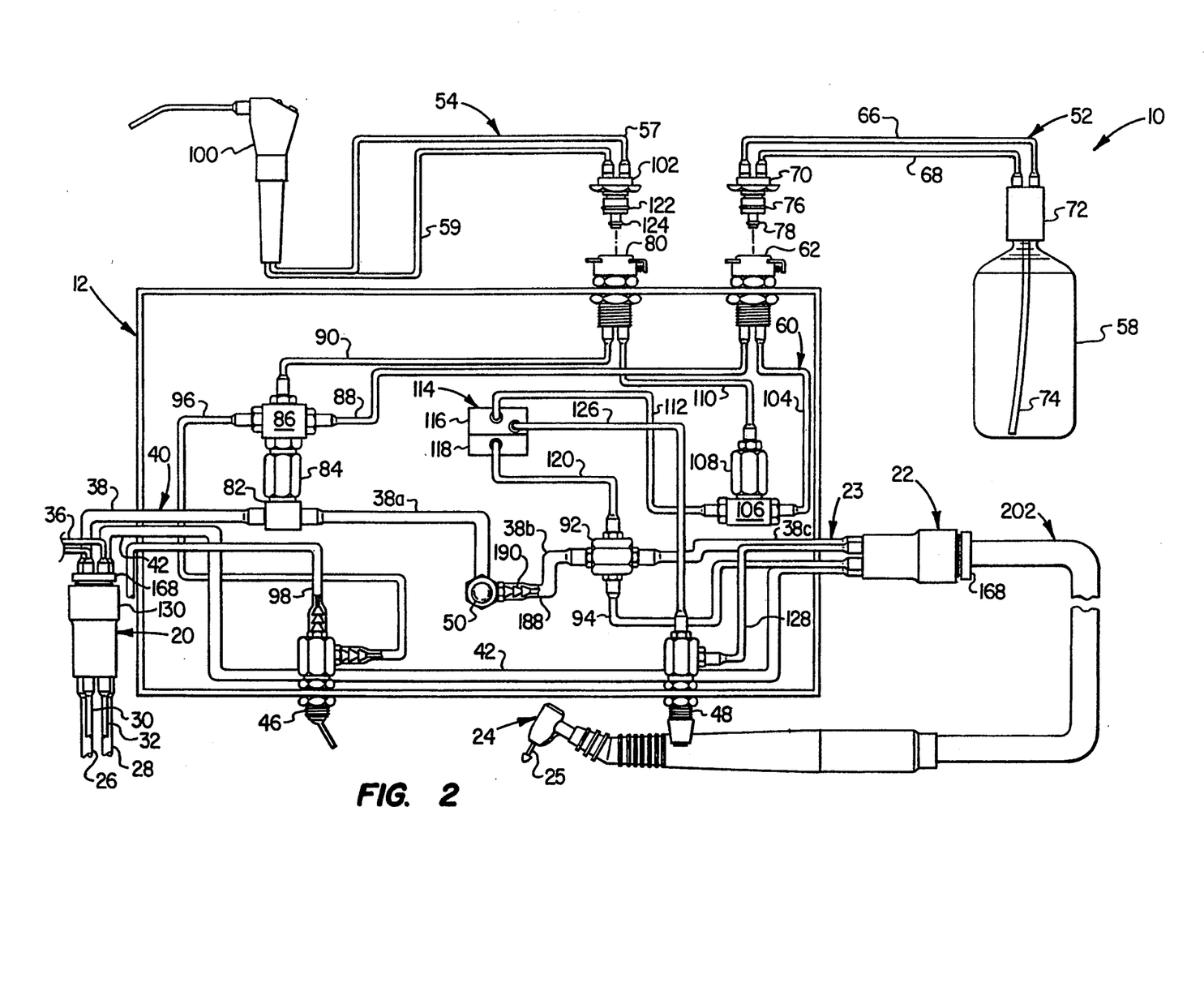
FIG. 2 is a plan view of the control box of FIG. 1 showing the attachment of conventional operating air, a sterile water bottle assembly, a dental syringe and a dental handpiece attached thereto.

A portable sterilizable apparatus for delivering substantially sterile operating fluids to dental appliances is indicated generally by the reference numeral 10 in FIGS. 1 and 2. A sterilizable portable control box 12 in FIG. 1 has a box 14 having an open top which is closed by cover 16 which is removably fastened with fasteners 18. Box 14 has a series of vent openings 15 in the rear wall to permit egress of steam or gas for sterilization. Extending from the left hand side of control box 12 is an air supply connector for pressurized operating air generally designated by the reference numeral 20. Connector 20 should be understood as a conventional standard connector having lines which lead to the master dental control unit, where the air pressure is modulated by a foot rheostat (not shown) that is operable by the dentist and is available as standard equipment at most dental operating stations. Extending from the right hand side of control box 12 is a connector similar to connector 20, generally described by reference numeral 22. Connector 22 is in fluid communication in a manner to be described, with tubing branches leading in part from connector 20. Connector 22 is in fact a dental appliance fitting for detachably engaging a dental appliance 24 in FIG. 2, shown to be a dental handpiece. A fitting 80 (FIG. 2) for another dental appliance, namely dental syringe 100 is mounted in the rear wall of box 12 with air and sterile water connections through tubing harness 54 shown in FIG. 1.

Air supply connector 20 has a main air supply branch 26 and an air return tube 28. The tubing harness of connector 20 also includes a chip air tube 30 and a water supply tube 32. However, for purposes of the invention, chip air tube 30 communicates through connector 20 with exhaust tube 34 and water supply tube 32 communicates through connector 20 with exhaust tube 36 which are shown primarily for illustration of the fact that the chip air and water supply through the conventional tubing harness are not employed. Chip air and water would preferably be shut off back at the master dental control unit so that only pressurized operating air is supplied to the control box through air supply connector 20.

Operating air from supply tube 26 is supplied through connector 20 to a main branch tube 38 of an internal air supply network referred to generally by the reference numeral 40. Internal air supply network 40 includes all the air passageways and connecting fittings that are internal to box 12. Main air supply tube 38 is continued by segments to be further described, that lead in fluid communication through connector 22, harness 202 and ultimately to drive the turbine of dental handpiece 24. The drive air from handpiece 24 is returned through another tube in harness 202 through connector 22 and return air branch 42 in fluid communication with connector 20. Return air branch tube 42, a part of internal air supply network 40, is in fluid communication with air return tube 28 through connector 20.

The front panel of the control box includes an adjustable needle valve 48 and vent control switch 46. Vent tube 98 is provided to selectively vent a portion of the air from air supply network 40 in cooperation with control switch 46. This allows, after venting, the removal of the tube fittings 102 and 70 and the cap 72 of the water supply bottle. The top cover includes an off/on air foot control switch 50. Extending from the back panel of control box 12 is a tubing harness for a sterile water supply bottle generally designated 58 and a tubing harness for another dental appliance generally designated by the reference numeral 54. Extending from dental appliance fitting 22 is a tubing harness for dental appliance 24 generally designated 202.

FIG. 2 shows a plan view of the system with cover 16 of box 12 removed. At the heart of the system is a separately sterilizable water supply bottle 58 which is fluidly coupled with an internal water supply network 60 in the control box through water supply fitting 62. Internal water supply network 60 includes all the water passageways and connecting fittings that are internal to box 12. Water supply fitting 62 is mounted in the rear panel of the control box. Tubing harness 52 delivers water and air to water supply fitting 62 through a water supply tube 66 and an air supply tube 68. An end portion of tubing harness 52 has a detachable connector 70. An opposite end portion of harness 52 has a removable cap 72 for sterile water bottle 58. Water supply tube 66 is fluidly coupled with depending entry tube 74 extending to the bottom of bottle 58 through which water is delivered to tube 66 when the water bottle is pressurized by operating air by means of tube 68. Connector 70 has "O" rings 76,78 in separately defined portions which seal against internal portions of water supply fitting 62 and cooperate therewith to fluidly communicate air through tubing 68 and water through tubing 66 in a quick connect and disconnect fitting. Mounted in the rear wall panel of box 12 alongside fitting 62 is an identical fitting 80 for another dental appliance. Thus it may be seen that bottle 58 and harness 52 are in fluid communication, through detachable connector 62,70, with internal fluid supply network 60 in the control box, in order to supply sterile water from bottle 58 through tube 66 in response to operating air pressure that may be supplied through air supply tube 68 through a connection with air supply network 40.

Internal air supply network 40 has a main air supply tube 38 in fluid communication with connector 22 through main air tube sections 38a, 38b, and 38c. Tubing 38,38a are connected through tee 82 having one-way flow valve 84 connected thereto for passage of air into four-way junction 86. Junction 86 has a first secondary branch tube 88 through which operating air from tube 38 passes into water supply fitting 62. When tubing harness 52 is fluidly coupled with water supply fitting 62, the air from branch 88 passes through air supply tube 68 and cap 72 to pressurize the water in bottle 58 so that it can be supplied to internal water supply network 60 through collection tube 74 through tube 66 in harness 52.

Junction 86 also has connected thereto a second secondary branch tube 90 which at the opposite end is connected to fitting 80 for the supply of operating air to another dental appliance. Simultaneously, main drive air is supplied through tubing 38a, switch 50, tube 38b, tube 38c, connector 22 and tubing harness 202 to supply drive air to dental handpiece 24. One end of main air supply tubes 38b and 38c is connected to another four-way junction 92 for passage of drive air therethrough. Junction 92 has a chip air branch 94 in fluid communication with dental handpiece 24 through connector 22 and tubing harness 202. Chip air is supplied in order to blow away debris caused by drill burr 25.

Internal air supply network 40 includes a selective means for venting pressurized operating air from sterile water bottle 58 so that operating pressure can be removed from the bottle as desired for removal of cap 72 and the fittings 102 and 70. This comprises a vent tube 96 fluidly coupled between junction 86 and toggle switch 46 to exhaust vent tube 98 which leads outside the control box to atmosphere. Junction 86 is connected to the main air supply through the one-way flow valve 84. Valve 84 is adapted to permit air flow to the junction but retain air pressure in the junction and first and second secondary air branches in order to keep the water bottle 58 pressurized with residual pressure after the supply of operating air to the control box has been interrupted. By opening toggle switch 46 between vent tube 96 and exhaust vent tube 98, residual pressure can be relieved to depressurize the sterile water bottle 58 as desired. Retained pressure will be vented simultaneously from dental syringe 100 which is connected through tubing harness 54 by means of a quick connector 102 and fitting 80. This has the advantage of permitting the dispensing of an ounce or two of sterile water from bottle 58 through dental syringe 100 at the completion of a dental operation even after the main air supply at tube 38 has been shut off.

Returning now to internal water supply network 60, it will be noticed that all the sterile water is supplied through tube 104 connected between water supply fitting 62 and tee 106. Branch tube 112 leading from tee 106 is in fluid communication with a normally closed air operated pilot valve 114 having a water chamber 116 and an air chamber 118 which is activated or opened by depression of a diaphragm in air chamber 118. The diaphragm depresses a valve that controls the flow of sterile water from the sterilizable water bottle through the pilot valve. Air is supplied to pilot valve 114 by means of branch tube 120 leading directly from junction 92. Air to junction 92 and branch tube 120 is selectively controlled by air control switch 50. Switch 50 simultaneously controls the flow of air in the main drive air tube 38a, branch tube 120 and tube 94. This sterilizable air actuated pilot valve 114 can be obtained from American Dental Accessories, Inc. (ADI) of Newberg, Oreg., and utilizes a VITON ™ diaphragm.

Sterile water is supplied to dental syringe 100 via tee 106, one-way flow valve 108 and syringe branch 110 in fluid communication with connector 80. Connector 80 is a quick-connect and disconnect fitting which engages connector 102 having "O" rings 122,124 which separate the air and water from branch tubes 90, 110 so that the water supplied from tube 110 through connector 80 and connector 102 is in fluid communication with syringe 100 through tube 57 leading to the syringe. Air from second secondary branch 90 is in fluid communication through connector 80 and connector 102 with syringe 100 through tube 59 leading to the syringe. Water supply tube 110 may be referred to as the syringe branch and second secondary branch 90 may be referred to as the syringe air branch. One-way flow valve 108 connected to tee 106 and syringe branch 110 is adapted to prevent reverse flow from syringe 100 so that internal water supply network 60 cannot be contaminated by backflow from the dental syringe. The flow is always in one direction under pressure and nothing can enter the sterile water network by backflow through one-way flow valve 108.

Finally, water chamber 116 of pilot valve 114 has a coolant branch 126 in fluid communication with needle valve 48 which has an outlet leading to coolant tube 128. Coolant tube 128 is in fluid communication with connector 22, harness 202 and dental handpiece 24 in order to supply sterile cooling water in the vicinity of a grinding attachment 25 on the dental handpiece in order to cool the work area being operated on. The needle valve is used to adjust the flow of coolant so that a sufficiently fine mist or a spray is provided to the work area, which is always in the vicinity of grinding attachment 25.

FIG. 3 shows the details of connectors 20 and 22 which for convenience will be discussed with respect to connector 20. Sleeve 130 has a threaded upper portion 132 and a reduced diameter lower portion 134 with a ledge 136 separating the two. Slidingly fitted into sleeve 130 is a body 138 having a rim 140 which rests on ledge 136 in assembly. The lower end of body 138 has barbed tube connectors 142,144,146,148 with centralized openings, extending axially from body 138. The openings extend axially through the length of body 138 and terminate respectively as openings 150,152,154,156 in the upper face of body 138. Rim 140 and the upper transverse face of body 138 define a sealing surface for a gasket 158 having respective openings 160, 162, 164, 168 which are aligned with and seal openings 150,152,154,156 when gasket 158 is assembled against the sealing surface. A threaded end connector 168 for a tubing harness 202 has hollow stems 170,172,174,176 which respectively align with and pass through openings 160,162,164,166 of gasket 158 and openings 150,152,154,156 of body 138.

When sleeve 130 is slipped over body 138 until rim 140 rests on ledge 136, it may be rotated relative to body 138, gasket 158 and threaded end connector 168 which are drawn together with the stems in the respective openings. When the threads are engaged to pull the lower face of connector 168 against the gasket and the gasket 158 against the upper face of body 138, tightening the sleeve by further rotation sealingly secures the end connector and body to form leak-proof passages for air and water. The leak-proof passages may be continued through threaded end connector 168 to terminate in respective tubing barbs for attachment of a tubing harness 202 which may be arranged within a protective sheath 178. Respective tubing barbs 180,182,184,186 are aligned with stems 170,172,174,176.

Figures 4, 5:
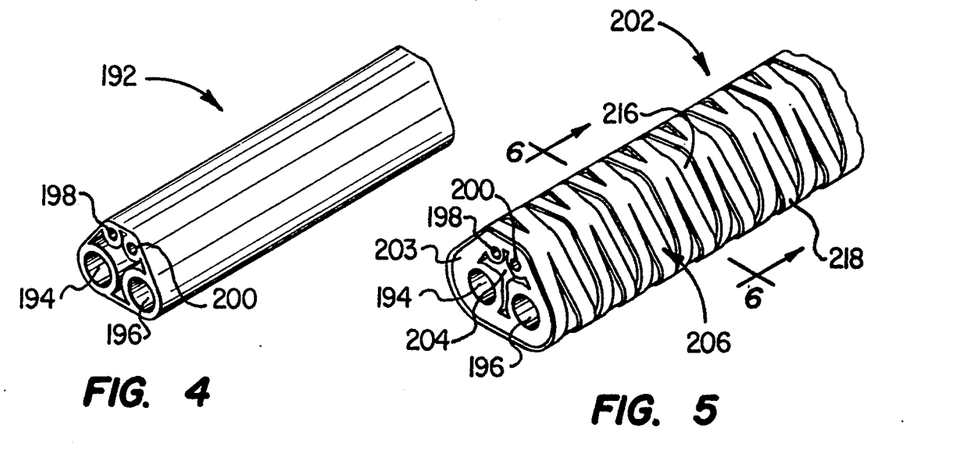
FIG. 4 is a perspective view of conventional 4-hole tubing harness that is used to connect a dental handpiece with the air and water supply.
FIG. 5 is a perspective view of a 4-hole tubing harness of the invention modified to be fabricated from silicone or other high temperature rubbers which can be sterilizable in an autoclave and connectable with a standard 4-hole connector in the same manner as the conventional tubing harness.

The output end of connector 20 is in fluid communication through tube barbs 180,182,184,186 with about a 3 foot section of sterilizable sheathed tubing harness 202 shown in FIG. 5. The other end of this section is separated into four individual tube ends by severing quadrants through cross-shaped hollow 204. Since the invention does not use conventional chip air and coolant water coming from tubes 30,32 the split off tubes containing openings 198,200 can be directed into exhaust tubes 34,36 or plugged off on the input side. The split off tube portion containing operating air opening 194 is preferably sheathed from the short distance from the split to the barb connection at 82 in a manner similar to FIG. 8. Return air tube 196 is similarly sheathed for a short distance and then is connected to a straight through tube barb which is then connected to return air line 92 for reasons of economy as will be explained later. The bulk of all the tubes within the control box can be made of a less expensive autoclavable material. The straight through tube barbs are not shown but are merely opposed barbs with an opening through the middle. In the case of connector 22, tube barb 184 is connected to the main operating air tube delivering drive air to the dental handpiece 24 through tubing harness 202 and tube barb 186 is connected to the return air tube coming from the dental handpiece 24 through tubing harness 202.

It is imperative that fluid from the coolant spray opening in the dental handpiece be controlled by means which permit coolant to flow, as adjusted by the needle valve, when main drive air is being supplied to the dental handpiece and to shut off when drive air is shut off. At the same time, the control means for coolant fluid must not permit backflow into the sterile water supply in internal water supply network 60. Both of these functions are provided by pilot valve 114, switch 50 and/or the foot control that starts and stops the flow pressurized operating air in tube 38 through connector 20 and air supply tube 26 to operate the dental handpiece.

Once tube 38 is pressurized, air flows through one way flow valve 84 into junction 86 and pressurizes the air lines leading to bottle 58 and syringe 100 as long as toggle switch 46 is closed. Operating air pressure is retained in this part of the air supply network even if the supply to tube 38 is shut off and the pressure leaked to atmosphere. As fax as the dental handpiece is concerned, zero operating pressure can also result from closing of switch 50 even if there is still pressure in tube 38,38a. The retained operating pressure means that sterile water in pilot valve water chamber 116 remains under positive pressure even when the operating air supply is cut off by either not depressing the foot rheostat pedal or by closing foot switch 50. Without activation air pressure applied through tube 120 to air chamber 118, the valve in water chamber 116 stops the flow of sterile water. Because the water supply in tube 112 is always under pressure, there is no backflow into the sterile water supply.

Operating air pressure in junction 92 or absence thereof becomes the determining factor for operation of dental handpiece 24. When operating air is supplied to junction 92, it simultaneously flows through pilot branch 120 to air chamber 118 of valve 114. Valve 114 is a normally closed air activated water relay valve which isolates the air and water supply networks from each other. Air pressure in pilot branch 120 depresses a diaphragm in air chamber 118 which in turn depresses a valve in water chamber 116 which allows water to flow from tube 112 to 126 and pressurized sterile coolant fluid is supplied to dental handpiece 24 simultaneously with drive air pressure through tube 38c. When a conventional foot pedal rheostat connected to the master dental control unit is depressed, drive air is released which turns the turbine in the dental handpiece 24 and drives the drill burr. Sterile coolant mist is simultaneously expelled from the vicinity of drill burr 25. When the foot pedal rheostat on the master dental control unit is not depressed, the drill is stopped and the flow of coolant mist and chip air are also stopped. If the operating air pressure at junction 92 is shut off, as by closing switch 50, the pressure in pilot branch 120 is reduced to atmospheric and the supply of coolant to the handpiece ceases because the air is no longer depressing the diaphragm in the air chamber 118 and so the diaphragm is no longer opening the spring loaded valve in the water chamber. This also keeps the rest of the sterile water system pressurized in air activated pilot valve 114. Thus, handpiece 24 is simultaneously supplied with operating air, sterile water and chip air or with nothing, depending on the pressure status at junction 92. The pilot valve is a control means in fluid communication with the operating air supply to the dental handpiece so that air and sterile coolant water are both either on or off.

In operation, the emphasis is on a compact unit which is easily manually portable, which will directly connect to an installed dental unit which all dentists utilize, which has a separately sterilizable water supply which holds sufficient sterile fluid for a typical dental operation, a separately sterilizable dental handpiece and tubing harness, and a separately sterilizable dental syringe and tubing harness. The control box is only about 6" long, 3½" wide and 2⅜" high. The control box also has vent slots in the back of the box to allow sterilizing steam or other sterilizing vapors to enter in and around the air and water tube networks during sterilization cycles.

A particular advantage is provided by threaded end connector 168 and the associated parts shown in FIG. 3 which enable control box 12 to be utilized with conventional sleeve 130 and body 138 which are conventional connections for a dental handpiece illustrated as connector 20 in FIG. 1. A similar connector 22 is used to connect and disconnect the tubing harness of a dental handpiece 24 from control box 12. Handpiece 24 is separately sterilizable. Dental syringe 100 and water bottle 58 are separately sterilizable and connected to control box 12 with quick connect fittings. It is anticipated that the tees and junctions will be made with sterilizable electroless nickel plated brass or stainless steel, as will the quick connect fittings 80,102, and 62,70.

In order to obtain an apparatus which is sterilizable in an autoclave, materials must be selected with care. Autoclaving means exposing the control box, handpiece, syringe, and water bottle and their associated tubing harnesses to steam of at least 250° F. for at least 15 minutes at 15 psi. Standard dental tubing and fittings will not withstand these severe conditions which are necessary to protect against possible contamination by bacterial or viral agents. The main air drive tubes 38,38a,38b,38c and the return air tube 42 have a lumen of ¼". Tee 82, switch 50, and pilot junction 92 have barbed tubing connectors which are sized to sealingly accept tube with a lumen of about ⅛". For example, the end of tubing 38b is cut away at 188 to show a barbed connection 190 to switch 50. These tubes are also fitted with crimped metal clamps to hold them in place.

The remainder of the air and water tubes have a lumen of approximately 1/16" and an outside diameter of approximately 3/16" and they are connected to the respective fitting tees, junctions and pilot valve 114. These smaller diameter tubes are connected to the fittings and connectors with suitably sized barbed connectors as illustrated by the cutaway portions of tubes 96 and 98 where they are connected to toggle switch 46. All of these barbed connections have crimped metal clamps over the tubes which are appropriately sized to hold the tubes and barbed connections together. FIG. 4 shows a conventional 4-hole tubing harness 192 used to interconnect the conventional 4-hole connections of a dental handpiece and the tubing harness leading from the foot control which supplies operating air and water, chip air and returns used air. This tubing harness is usually extruded as one piece in the shape shown. It has openings 194,196,198,200 respectively for operating air, return air, cooling water and chip air. However, the conventional plastic will not withstand autoclaving without melting or otherwise deteriorating.

FIG. 5 shows a preferred form of 4-hole tubing harness 202 in which the body 203 is extruded from silicone rubber which will withstand autoclaving repeatedly and preferably has a "Shore" hardness on the "A" scale of about 60 or higher. It has the same openings designated 194,196,198,200 as did the conventional 4-hole harness. This is a relatively soft, very flexible material. Body 203 has a confluent outer wall that is thicker than the molded in tubes of connections harness 192. An outer wall of at least 0.080 inches is preferred in order to have a ratio of burst/operating pressure of about 4 to 1 at about 40 psi which is obtained with the aid of the adjacently placed similarly pressurized internal tube walls of tubes 194,196,198,200 but mainly from the expanded tubing cover 206.

Figures 6, 7:
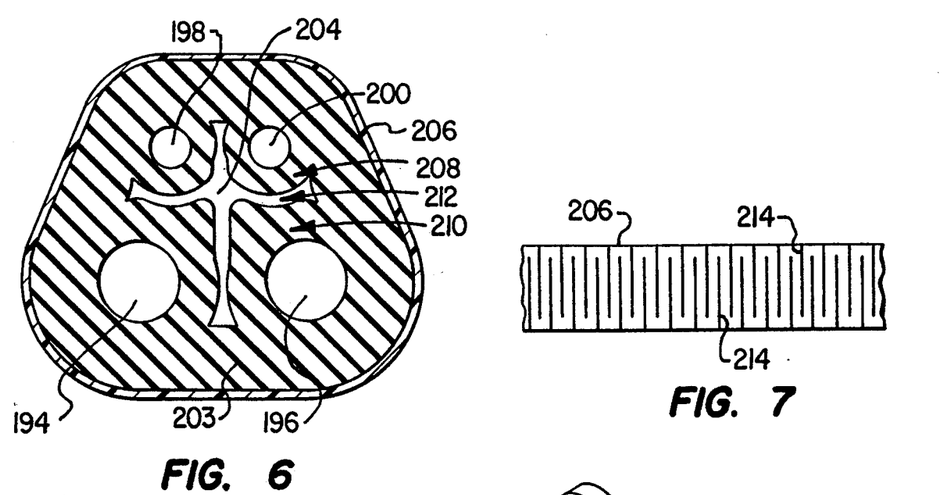
FIG. 6 is a cross-sectional view of the modified tubing harness of FIG. 5 on lines 6—6.
FIG. 7 is a plan view of the special tubing harness covering showing how it is fabricated before installation.

FIG. 6 shows the cross section of special tubing harness 202. The spacing of openings 194,196,198,200 must be the same as FIG. 4 so that the tubing harness will retrofit conventional 4-hole connectors as must the entire width of tubing harness 202. Because the preferred silicone rubber is not as resistant to internal pressure as the conventional material, a special shape is extruded which is further supported against bursting by the expanded heat shrunk TEFLON ® covering of sheath 206. Preferably the openings have a slightly smaller diameter than the lumen of the large (⅛") and small (1/16") tubes so that the harness will have good resilient retention on the connector tubing barbs to hold it in place. Also, the smaller lumens can be utilized due to the natural lumenal expansion seen with silicone when pressure is applied internally. These smaller holes also make the silicone tube 203 smaller in width so that the TEFLON ® sheath 206 can be placed over tube 203 and still have a tubing harness 202 narrow enough in width to retrofit conventional dental equipment.

Internal hollow space 204 is formed roughly in the shape of a cross with a vertical stem and lateral arms of a width selected to accommodate some expansion caused by internal pressure in openings 194–200, facilitate insertion of tubing barbs and to allow splitting apart of the individual tubes. The gap in space 204 and the thickness of the internal walls of the tubes is selected to resist the desired pressure. In an exemplary arrangement, the internal wall 208 of the smaller tubes having openings 198,200 is about 0.03 inches and internal wall 210 of the larger tubes having openings 194,196 is about 0.05 inches with a gap between them of about 0.008 inches. Thus when the tubes 194–200 are subjected to internal pressure they can expand slightly and provide internal support to each other without bursting. The hollow "cross" 204 makes it easy to separate the end of body 203 into four individual irregular shaped tubes for connection to individual tube barbs. This feature permits a short three or four inch section of tubing harness 202 to be used at the place indicated as 23 in FIG. 2 where one end is connected to connector 22. The individual lines 38c,94,128 and 46 can have a section cut out and connected to the individual tubes split away from the end of body 203 along the arms of the "cross". The sheath covered ends of the respective tubes are connected to the remainder of tubes 38c,94,128,46 by means of straight through tube barb connectors (not shown). This permits a less expensive tube material to be used within the control box as will be explained below.

Figure 8:
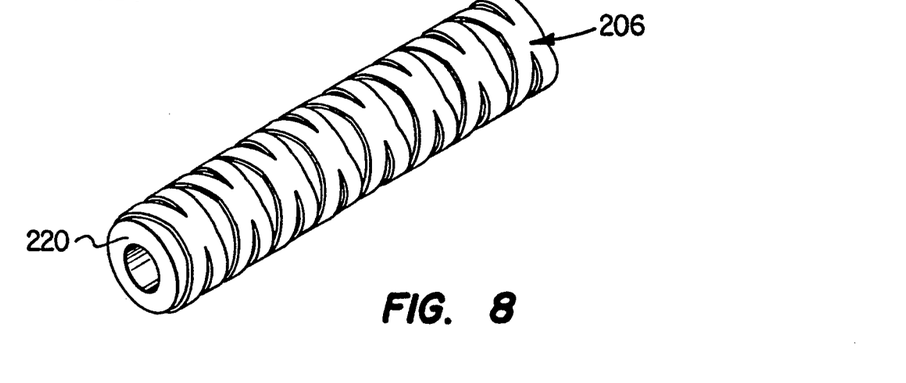
FIG. 8 is a perspective view of a single tube sterilizable by autoclaving which has a shrunk fit covering to prevent bursting of the underlying tube under pressure and also permit bending.

Outer sheath 206 is formed from flattened FEP heat shrunk TEFLON ® tubing, preferably having about 0.02 inch wall thickness. Equal length alternating opposing cuts 214 through both walls are perpendicular to the length and parallel to the width. The tube sheath will be slightly larger than the circumference of body 203 so as to slide over it lengthwise. Each cut is preferably about 3 millimeters from the previous opposing cut leaving about 2.5 millimeters of uncut flattened width. The completed sheath is unflattened and slid over the entire length of body 203 whereupon it is stretched lengthwise to open a regular pattern of gaps 216 and bands 218 so that there is about 1–1.5 millimeters of space at the widest aspect of the opposing cuts in the FEP TEFLON ® tubing. This assembly is subjected to dry heat of at least 350° F. for enough time (2–3 minutes) to allow the FEP tubing to shrink tightly against body 203. Appropriately sized expandable FEP TEFLON ® sheaths are used over the irregular shaped individual tubes separated from an end of body 203 in the same manner as FIG. 8 to provide short pressure resistant connections to the straight through tube barbs preferably used inside the confines of the control box 12. FIG. 8 shows the same construction as FIG. 5 except that an expandable sheath or cover 206 has been installed in the same manner as described above to prevent bursting of a circular shaped silicone rubber tube 220. This makes a repeatedly autoclavable tube that can be used between connections if desired.

A particular advantage for the special construction of the tubing harness of FIG. 5 and the tube of FIG. 8 is that it permits the tubing to be easily and flexibly bent without affecting its ability to retain internal pressure. This is particularly true where sharp bends are required and to permit the dental handpiece to be moved around in use. Where straight or nearly straight sections of tube are employed without bending, a solid uncut shrink fit FEP TEFLON ® sheath can be used. The silicone tubing can be obtained from New Age Industries of Willow Grove, Pa., and the FEP thermally reducible TEFLON ® sheathing material from Zeus Industrial Products of Orangeburg, S.C. The FEP TEFLON ® resin used to make the shrink fit sheath is normally made from DuPont FEP100 or FEP160 grade flurocarbon copolymer resin. The properties of typical materials are listed on Zeus and DuPont data sheets submitted with this application. The material will withstand continuous use at 400° F. and is heat shrinkable at about 350°–400° F. TEFLON ® is a trademark of EI dupont de Nemours, Inc.

It is preferable to use a less expensive but much thicker walled autoclavable tubing for the internal connections of the internal water and air supply network within sterilizable control box 12 and tubing harnesses 54 and 52 because the silicone rubber and TEFLON ® sheath combination is significantly more expensive than other available materials and the less expensive material does not have to have the TEFLON ® sheathing, thus making the fabrication much easier. Exemplary of a tubing material that will withstand repeated autoclaving without noticeable deterioration is a material sold under the trademark SANTOPRENE TM which is a resilient flexible synthetic rubber supplied by Monsanto Polymer Products Chemical Company and fabricated by Hudson Extruders, Inc. of Hudson, Ohio. It has the desirable high temperature resistance necessary to withstand typical autoclaving temperatures and is approved by the U.S. Food and Drug Administration (FDA).

In the dental art tubing with a lumen of ¼" has a ¼" outside diameter which means the wall is only 1/16" thick. If it is desired to have an operating pressure of 30–35 psig which is only 20% of burst pressure (safety factor of five), it will be necessary to increase the wall thickness of the main air drive and return tubes made of the SANTOPRENE TM material to ⅛" thick with a ⅜" outside diameter. Although FDA approval of dental water transporting class IV components is not essential, it is a desirable feature that is preferred.

Quick fittings 80,102 and 62,70 are a special order item made of electroless nickel chrome plated brass in the "Twin Tube" design with VITON ® seals from Colder Products Company of St. Paul, Minn. VITON ® is a high performance synthetic rubber referred to as a fluorocarbon and sold by the dupont de Nemours Company. This synthetic rubber, VITON ®, is utilized due to its superior resistance to chemical attack and its high temperature resistance allowing it to be repeatedly autoclaved.

Valves and switches 46,48,84,50,114,48 and 108 may be obtained with the same above-mentioned VITON ® seals and "O" rings from American Dental Accessories, Inc. (ADI) of Newberg, Oreg. All standard plastic parts like push button 50 and toggle switch 46 can be interchanged with metal components by the same ADI company as special order items.

It might be mentioned that commonly available silicone rubbers are suitable for the seals in the dental appliances and connectors and for the air and water tubing. It has good flexibility, resilience and resistance to high autoclaving temperatures and is available in FDA approved formulations.

The sterilizable water bottle may be glass or preferably a one liter autoclavable heavy duty plastic bottle which is fabricated from an enhanced crystalline homopolymer polypropylene by Nalge Company, Rochester, N.Y. It should withstand a standard operating pressure of 50 psig and be able to be repeatedly autoclaved at temperatures of up to 275° F. at up to 40 psi for up to one hour and be made of an FDA approved material.

The sterilizable air/water syringe is a special order item due to the fact that all the rubber gaskets and "O" rings are interchanged with silicone or VITON ®. Also, the standard plastic yellow and blue inserts next to the activation push buttons are replaced with a stamped imprint of "W" and "A" to indicate which button activates the water and which activates the air. This change is due to the fact that the yellow and blue plastic inserts will melt. This special order item is fabricated and obtainable from Forest Medical Products of Hillsboro, Oreg.

The custom male fitting 168 can be manufactured at several advanced machine shops and can also be manufactured by Forest Medical Products of Hillsboro, Oreg. It has a body 191 and can be fabricated from aluminum, electroless nickel plated brass or stainless steel. The thread configuration found on body 191 is 0.555-36 UNS-2A with a minor diameter of 0.525–0.532 and a pinch diameter of 0.5370–0.5424. This thread configuration must be long enough to fully engage the standard Midwest style "4-hole" connector nut 130 utilized to connect the female "4-hole" connector 138 to this above custom fitting male "4-hole" connector. This threaded portion may extend longer than is necessary but must be at least 0.315". Four holes are drilled through body 191 of custom male "4-hole" connector 168 with the hole corresponding with 174 having an internal diameter of approximately 0.153" and the hole corresponding with 176 having an internal diameter of approximately 0.185". The two upper, smaller holes corresponding with 170 and 172 have internal diameters of approximately 0.049". Body 191 has a diameter of approximately 0.577". The two smaller, upper holes would have syringe type thin walled stainless steel tubing with an outer diameter of approximately 0.049" extending approximately 0.245" out of the body 191 and press fit into the above mentioned two upper holes. Tube 176 preferably has an outer diameter of approximately 0.153" and an inner diameter of approximately 0.125" with a wall of approximately 0.014". Tube 174 preferably has an outer diameter of approximately 0.135" and an inner diameter of approximately 0.125" and a wall of approximately 0.005". These two lower tubes should protrude out of body 191 approximately 0.310" for tube 176 and 0.375" for tube 174 and press fit into the appropriate holes.

The two upper stainless steel tubes 170 and 172 should exactly index into holes 150 and 152 respectively of fitting 138. The two lower, larger stainless steel tubes 174 and 176 should exactly index into holes 154 and 156 respectively of fitting 138. On the reverse end of body 191, the two upper holes will be larger with the ability to press fit two single barbed stainless steel barbs. The two lower holes will be smaller with the ability to press fit two single barbed stainless steel tubes. Double barbed connectors 192 and 193 found in cap 72 of water bottle 58 are fabricated of electroless nickel plated brass and can be purchased from Beswick Engineering Co., Inc., of Ipswich, Mass.

What is claimed is:

1. A portable heat sterilizable dental apparatus useable at a conventional dental operatory station for delivering sterile operating fluid and operating air to dental appliances, comprising:

a separately heat sterilizable sterile water bottle and tubing harness connected thereto having air and water flow passages;

a compact portable heat sterilizable control box having:

an internal water supply network and an internal air supply network, said separately heat sterilizable sterile water bottle and tubing harness being detachably connected to the internal water supply network and internal air supply network through air and water flow passages in said tubing harness, a water supply fitting connected to said internal water supply network, said water supply fitting mounted on said control box being detachably connected to said tubing harness, means for detachable connection of the internal air supply network with an air supply connector of a conventional dental operatory station to deliver intermittent pressurized air to the internal air supply network by intermittent operation of a standard foot control, and means for connection to the standard connector of at least one detachable dental appliance, said means for connection being connected to said internal water supply network and said internal air supply network to supply sterile water from said sterile water bottle through said internal water supply network and operating air from said internal air supply network;

said apparatus being specially adapted to withstand heat sterilizing and subsequent application of conventional operating pressure and being suitable for passage of water in conformance with regulations for dental water, said apparatus including said compact control box, said internal air and water supply networks, said water supply fitting, said sterilizable water bottle and tubing harness, said means for connection and said means for detachable connection, all being repeatedly heat sterilizable at a temperature of at least 250° F. and useable for delivering sterile water to a patient during dental operations.

2. The apparatus of claim 1 wherein the internal air supply network includes a branch tube leading to the water supply fitting for supplying operating air and a selective means for venting pressurized operating air from the sterile water bottle so that operating air pressure can be removed from said bottle as desired.

3. The apparatus of claim 1 wherein the internal water supply network includes a sterile water supply tube leading to the means for connection to the standard connector of at least one detachable dental appliance having a one-way flow valve to permit water supply to said appliance while blocking reverse flow into the internal water supply network.

4. The apparatus of claim 1 wherein a dental handpiece is detachably connected through said means for connection to the standard connector of at least one detachable dental appliance, directly to the air supply network and indirectly to the water supply network through a pilot valve operated by the internal air supply network.

5. The apparatus of claim 4 further including a sterilizable dental syringe, said means for connection to the standard connector of at least one detachable dental appliance includes a mounted on said control box connection for said dental syringe fluidly connected to said internal water supply network.

6. The apparatus of claim 1 wherein the tubing harness of said sterilizable water bottle is made of a flexible high temperature resistant rubber tubing that will withstand repeated heat sterilization without noticeable deterioration.

7. The apparatus of claim 6 in which the internal air supply network and internal water supply network of the control box are made of flexible high temperature resistant rubber tubing that will withstand repeated heat sterilization without noticeable deterioration.

8. The apparatus of claim 7 wherein said fittings for water supply and said means for connection to the standard connector of a detachable dental appliance have flexible high temperature resistant rubber seals that will withstand heat sterilization without noticeable deterioration.

9. The apparatus of claim 6 including a sterilizable dental handpiece having a sterilizable tubing harness detachably connected through said means for Connection to the Standard connector of at least one detachable dental appliance being directly connected to said air supply network and to said water supply network for simultaneous supply of operating air and sterile water.

10. The apparatus of claim 9 wherein the sterilizable tubing harness for the sterilizable dental handpiece is made of a flexible high temperature resistant rubber tubing that will withstand repeated heat sterilization without noticeable deterioration.

11. The apparatus of claim 10 including a fitting for an air/water syringe having heat resistant seals, a sterilizable air/water syringe and a sterilizable syringe tubing harness detachably connectable to the syringe fitting, said air/water syringe fitting being interconnected with the internal air supply network and the internal water supply network, said sterilizable syringe tubing harness being made of a flexible high temperature resistant rubber tubing that will withstand repeated heat sterilization without noticeable deterioration.

12. The apparatus of claim 11 wherein said sterilizable dental handpiece and said sterilizable air/water syringe have seals that will withstand repeated heat sterilization without noticeable deterioration.

13. A portable sterilizable apparatus movable from dental station to dental station for delivering sterile operating fluids to dental appliances, comprising:

a sterilizable portable control box having a fitting for connection of pressurized dental operating air, an internal air supply network, an internal fluid supply network, a fluid supply fitting and at least one fitting for a detachable dental appliance;

said fitting for pressurized dental operating air being connected to said internal air supply network in said control box wherein said internal air supply network fluidly interconnects at least the fluid supply fitting and the at least one fitting for a detachable dental appliance in order to supply dental operating air;

a separately sterilizable fluid supply bottle having a tubing harness having an end portion detachably engageable with the fluid supply fitting of said control box and having air and liquid flow passages connecting said fluid supply bottle and said fluid supply fitting;

said control box having said internal fluid supply network fluidly interconnecting said fluid supply fitting and said at least one fitting for a detachable dental appliance through a pilot valve comprising an air activated water relay valve;

said at least one fitting for a dental detachable appliance being fluidly connected to said internal air and fluid supply networks to receive operating air from said internal air supply network and sterile fluid through said pilot valve from said fluid supply bottle;

wherein sterile fluid from said fluid supply bottle can be supplied to a dental handpiece through said at least one fitting for a detachable dental appliance in response to pressurized operating air applied to said air supply network, said flow of sterile fluid being controlled by operation of said pilot valve.

14. The apparatus of claim 13 including an adjustable needle valve wherein the flow of water to said at least one fitting for a dental appliance is adjustable by means of said adjustable needle valve.

15. The apparatus of claim 13 wherein the internal air supply network includes a branch leading to the fluid supply fitting, and a selective means for venting pressurized operating air from said fluid supply bottle so that operating pressure can be removed from said fluid supply bottle as desired.

16. The apparatus of claim 15 wherein the internal air supply network has a junction that supplies the branch leading to the fluid supply fitting, said junction also having a syringe air branch in fluid communication with said at least one fitting to a dental appliance to provide operating air to it syringe.

17. The apparatus of claim 16 wherein said junction is in fluid communication with a switch which simultaneously exhausts retained air pressure from said fluid supply bottle and said syringe air branch.

18. The apparatus of claim 13 wherein the internal fluid supply network includes a sterilizable water supply tube having a one-way flow valve which permits water supply to said at least one fitting for a dental appliance while blocking reverse flow into the fluid supply network.

19. A portable sterilizable apparatus for delivering substantially sterile operating fluids to dental appliances, comprising:

a sterilizable portable control box having a water supply fitting, a fitting for one detachable dental appliance, a fitting for another detachable dental appliance, an air supply connection for pressurized operating air, an internal air supply network in fluid communication with said air supply connection and an internal fluid supply network interconnected with said internal air supply network and said water supply fitting;

said internal air supply network having a main air branch in fluid communication with the fitting for said one detachable dental appliance through a junction having a first secondary branch in fluid communication with the water supply fitting for simultaneously supplying operating air to said fittings;

a separately sterilizable water supply bottle having a sterilizable tubing harness for delivery of sterile water through the tubing, the tubing harness having an end portion detachably engageable with the water supply fitting of said control box to establish water and air flow passages between the bottle and the control box;

said fitting for one detachable dental appliance being fluidly interconnected to said internal water supply network and being fluidly interconnected with said main air branch for delivering sterile water from said water supply bottle and delivering operating air;

said fitting for another detachable dental appliance being fluidly interconnected with said internal air supply network and having a connection with said internal fluid supply network through a one-way flow valve, thereby being adapted to deliver operating air and sterile water to a tubing harness of a dental syringe;

wherein sterile water from said water supply bottle and operating air may be delivered to said one and said another fittings for detachable dental appliances in response to pressurized operating air being supplied through the air supply connection when the tubing harness of the separately sterilizable water supply bottle is connected to the water supply fitting and whereby the apparatus can be disconnected from an operating air supply at one dental station and easily carried to another dental station for use.

20. The apparatus of claim 19 further including a separately sterilizable dental handpiece, tubing harness and fitting at the end of the tubing harness adapted for operable connection to said fitting for one detachable dental appliance on the control box.

21. The apparatus of claim 20 further including a separately sterilizable dental air/water syringe appliance, tubing harness and fitting at the end of the tubing harness adapted for operable connection to said fitting for another detachable dental appliance on the control box.

22. The apparatus of claim 19 wherein the control box includes control means interconnecting the internal air and water supply networks for simultaneously starting and stopping the flow of operating drive air and sterile water to said fitting for one detachable dental appliance and a dental handpiece when connected thereto, in response to turning the main air supply on or off.

23. The apparatus of claim 22 wherein that portion of the internal air supply network that supplies operating air to the sterile water supply bottle is connected to the main operating air supply through a one-way flow valve in said junction having a first secondary air branch that allows air to pressurize said bottle but retains the pressurized air after the main operating air is shut off so that pressurized sterile water remains available to said fitting for another detachable dental appliance.

24. The apparatus of claim 22 wherein the control means is a pilot valve operated by air pressure from the main air branch, which controls the flow of sterile water from the internal water supply network to said fitting for one detachable dental appliance.

25. A portable sterilizable apparatus movable from dental station to dental station for delivering substantially sterile operating fluids to dental appliances, comprising:

a portable control box detachably connectable to a conventional standard source of pressurized dental operating air, having a sterile water supply connector for a sterile water supply bottle and a connector for detachably connecting at least one dental appliance;

a separately sterilizable water supply bottle detachably connected to said sterile water supply connector extending from the control box, said water bottle being a sterilizable bottle having a sterilizable tubing harness having air and sterile water flow passages and a quick connector for detachably making air and sterile water connections with said sterile water supply connector extending from the control box;

the control box having an internal air supply network interconnected with an internal sterile water supply network, including means for simultaneously supplying operating air to the sterilizable water supply bottle and the connector for detachably connecting at least one dental appliance when the standard source of pressurized operating air is connected to the internal air supply network in the control box;

at least one sterilizable dental appliance which in use discharges water that contacts a patient's oral cavity, said appliance being detachably connectable to said connector for detachably connecting at least one dental appliance extending from said control box, having a water connection in fluid communication with said water supply bottle through said control box; and control means to selectively supply sterilized water to the dental appliance from the sterilizable water supply bottle through the control box.

26. The apparatus of claim 25 wherein the control means includes a pilot air operated relay valve having an air inlet connected to the air supply network, a water inlet connected in fluid communication with the connector leading to the sterile water supply bottle and a water outlet in fluid communication with the said connector for detachably connecting at least one dental appliance whereby sterile water is supplied to said at least one sterilizable dental appliance only when air is supplied to the pilot valve through the air supply network and the air supply to the pilot valve is in a common conduit in fluid communication with said sterilizable dental appliance so that air and water are both on or both off.

27. A portable sterilizable apparatus for delivering substantially sterile operating fluids to dental appliances, comprising:
   a separately sterilizable water supply bottle having a tubing harness for delivery of sterile water through the tubing, the tubing harness having an end portion detachably engageable with a water supply fitting of a control box having water and air flow passages between the bottle and the control box;
   a sterilizable portable control box having an air supply connection for pressurized operating air in fluid communication with an internal air supply network in the control box, the internal air supply network interconnecting at least the tubing harness of the water supply bottle and at least one dental appliance fitting for dectachably engaging a dental appliance, said control box having an internal fluid supply network interconnecting in fluid communication at least the water supply fitting and said at least one dental appliance fitting, the internal air supply network having a main air branch in fluid communication with said at least one dental appliance fitting and a junction having a first secondary branch in fluid communication with the water supply fitting for simultaneously supplying operating air to said water supply bottle and said at least one dental appliance fitting;
   wherein the main air branch has a junction with a pilot branch leading to a normally closed air operated pilot valve in the internal water supply network which controls the flow of sterile water from the sterilizable water supply bottle through the pilot valve to the at least one dental appliance fitting;
   wherein sterile water from the water supply bottle and pressurized operating air may be delivered to the at least one dental appliance fitting in response to pressurized operating air being supplied through said air supply connection and said normally closed air operated pilot valve when said tubing harness and said water supply fitting are interengaged and whereby the apparatus can be disconnected from an operating air supply at one station and easily carried to another station for use.

28. The apparatus of claim 27 wherein the main branch of the air supply network has a switch upstream of the pilot branch junction for starting or stopping the flow of air to the pilot branch to start or stop the flow of sterile water at the pilot valve.

29. The apparatus of claim 27 wherein the control box includes a one way flow valve between the pilot valve and water supply fitting in fluid communication with said another dental appliance fitting through said one-way flow valve adapted to permit water flow to said another dental appliance fitting but prevent backflow into the sterile water supply.

30. The apparatus of claim 29 wherein a junction having a first secondary branch is connected to the internal air supply network through a one-way flow valve adapted to permit air flow to the junction and retain the air pressure in the junction and first secondary branch to keep the water supply bottle pressurized with residual pressure after the supply of operating air to the control box has been interrupted.

31. The apparatus of claim 30 wherein the junction having the first secondary branch has a second secondary branch in fluid communication with said another dental appliance fitting to supply pressurized operating air through said another dental appliance fitting to a dental appliance that may be connected thereto.

32. The apparatus of claim 31 wherein the junction in the internal air supply network having the first and second secondary branches has a vent line which may be opened to relieve retained air pressure in order to depressurize the sterile water bottle.

33. The apparatus of claim 31 further including a flow adjusting needle valve wherein the flow of sterile water from the air operated pilot valve to said at least one dental appliance fitting passes first through said flow adjusting needle valve.

34. The apparatus of claim 32 wherein the main aid branch has a separate chip air branch in fluid communication with said at least one dental appliance fitting for supplying chip air to a dental appliance that may be connected thereto.

35. The apparatus of claim 34 further including a separately sterilizable dental handpiece, tubing harness and fitting at the end of the tubing harness adapted for operable connection to said at least one dental appliance fitting on the control box.

36. The apparatus of claim 35 further including a separately sterilizable dental syringe appliance, tubing harness and fitting at the end of the tubing harness adapted for operable connection to said another dental appliance fitting on the control box.

37. A method of providing substantially sterile water to a dental patient through the outlet of a dental appliance, comprising:
   providing a portable sterilizable control box connectable to a conventional source of dental operating air, at least one sterilizable water using dental appliance, tubing harness and connector for detachably connecting the tubing harness to the control box, and a sterilizable water bottle, tubing harness and connector for detachably connecting the tubing harness to a water connector in the control box;
   sterilizing the control box;
   sterilizing said water bottle, tubing harness and connector;
   sterilizing the dental appliance, tubing harness and connector;
   connecting the sterilized control box to a conventional source of operating air at a dental operating station;
   connecting the sterilized water bottle containing sterile water to the control box by means of the tubing harness and connector for the bottle;
   connecting the sterile water using dental appliance to the control box by means of the tubing harness and connector; and
   dispensing sterile water to a patient from the sterile water bottle through the control box and sterile water using dental appliance whereby a dental operation can be performed with a substantially sterile dental appliance and sterile water.

* * * * *